(12) United States Patent
Finlay

(10) Patent No.: US 10,196,382 B2
(45) Date of Patent: Feb. 5, 2019

(54) BIS-PYRIDAZINE COMPOUNDS AND THEIR USE IN TREATING CANCER

(71) Applicants: AstraZeneca AB, Sodertalje (SE); Cancer Research Technology Limited, London (GB)

(72) Inventor: Maurice Raymond Verschoyle Finlay, Cambridge (GB)

(73) Assignees: AstraZeneca AB, Södertalje (SE); Cancer Research Technology Limited, London (GB)

( * ) Notice: Subject to any disclaimer, the term of this patent is extended or adjusted under 35 U.S.C. 154(b) by 0 days.

(21) Appl. No.: 15/360,332

(22) Filed: Nov. 23, 2016

(65) Prior Publication Data
US 2017/0152244 A1    Jun. 1, 2017

(30) Foreign Application Priority Data
Nov. 27, 2015 (GB) .................... 1520959.6

(51) Int. Cl.
*C07D 403/14* (2006.01)
(52) U.S. Cl.
CPC ................. *C07D 403/14* (2013.01)
(58) Field of Classification Search
CPC .................................................. C07D 401/14
See application file for complete search history.

(56) References Cited

U.S. PATENT DOCUMENTS

2014/0142081 A1    5/2014    Lemieux

FOREIGN PATENT DOCUMENTS

| WO | 2013078123 A1 | 5/2013 |
|---|---|---|
| WO | 2015101957 A2 | 7/2015 |
| WO | 2015181539 A1 | 12/2015 |

OTHER PUBLICATIONS

Pinedo et al. (2000).*
McMahon et al (2000).*
Ajit, G., et al., "Small molecule glutaminase inhibitors block glutamate release from stimulated microglia", Biochemical and Biophysical Research Communications, Jan. 1, 2014, vol. 443, No. 1, pp. 32-36.

* cited by examiner

*Primary Examiner* — Paul V Ward

(57) ABSTRACT

A compound of Formula (I):

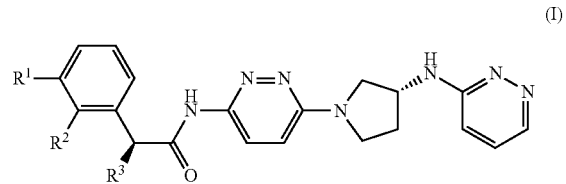

or a pharmaceutically acceptable salt thereof, where $R^1$ can be hydro, methoxy, difluoromethoxy or trifluoromethoxy; $R^2$ can be hydro, methoxy, trifluoromethoxy or trifluoromethyl; and $R^3$ can be hydro or methoxy. The compound of formula (I) can inhibit glutaminase, e.g., GLS1.

11 Claims, No Drawings

BIS-PYRIDAZINE COMPOUNDS AND THEIR USE IN TREATING CANCER

FIELD OF INVENTION

In accordance with 35 U.S.C. 119(a)-(d) and (f), 172, 365(a) and (b), 386(a) and (b), and 37 CFR 1.55 this application claims the benefit of GB Application No. 1520959.6 filed on 27 Nov. 2015.

The specification generally relates to bis-pyridazine compounds and pharmaceutically acceptable salts thereof. These compounds act on the glutaminase 1 enzyme ("GLS1"), and the specification therefore also relates to the use of such compounds and salts thereof to treat or prevent GLS1 mediated disease, including cancer. The specification further relates to pharmaceutical compositions comprising bis-pyridazine compounds and pharmaceutically acceptable salts thereof; kits comprising such compounds and salts; methods of manufacture of such compounds and salts; intermediates useful in the manufacture of such compounds and salts; and to methods of treating GLS1 kinase mediated disease, including cancer, using such compounds and salts.

BACKGROUND

Glutamine is the most abundant plasma amino acid and is involved in many growth promoting pathways. In particular, glutamine is involved in oxidation in the tricarboxylic acid cycle and in maintaining cell redox equilibrium, and also provides nitrogen for nucleotide and amino acid synthesis (Curi et al., *Front. Biosc.* 2007, 12, 344-57; DeBardinis and Cheng, *Oncogene* 2009, 313-324). Many cancer cells rely on glutamine metabolism as a consequence of metabolic changes in the cell, including the Warburg effect where glycolytic pyruvate is converted to lactic acid rather than being used to create Acetyl CoA (Koppenol et al., *Nature Reviews* 2011, 11, 325-337). As a consequence of this reliance on glutamine metabolism, such cancer cells are sensitive to changes in exogenous glutamine levels. Furthermore, there is much evidence to suggest that glutaminolysis plays a key role in certain cancer types (Hensley et al., *J. Clin. Invest.* 2013, 123, 3678-3684), and is associated with known oncogenic drivers such as Myc (Dang, *Cancer Res.* 2010, 70, 859-863).

The first step of glutamine catabolism to glutamate is catalysed by glutaminase, which exists as 2 isoforms GLS1 and GLS2, originally identified as being expressed in the kidney and liver respectively. Kidney glutaminase (GLS1) is known to be more ubiquitously expressed than liver glutaminase (GLS2), and has 2 splice variants, KGA and the shorter GAC isoform, both of which are located in the mitochondria. (Elgadi et al., *Physiol. Genomics* 1999, 1, 51-62; Cassago et al., *Proc. Natl. Acad. Sci.* 2012, 109, 1092-1097). GLS1 expression is associated with tumour growth and malignancy in a number of disease types (Wang et al., *Cancer Cell* 2010, 18, 207-219; van der Heuval et al., *Cancer Bio. Ther.* 2012, 13, 1185-1194). Inhibitors of GLS1 are therefore expected to be useful in the treatment of cancer, as monotherapy or in combination with other anti-cancer agents.

SUMMARY OF INVENTION

Briefly, this specification describes, in part, a compound of Formula (I):

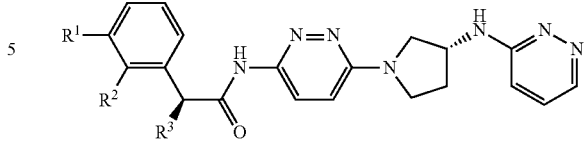

or a pharmaceutically acceptable salt thereof, where:
$R^1$ is hydro, methoxy, difluoromethoxy or trifluoromethoxy;
$R^2$ is hydro, methoxy, trifluoromethoxy or trifluoromethyl; and
$R^3$ is hydro or methoxy.

This specification also describes, in part, a pharmaceutical composition which comprises a compound of Formula (I), or a pharmaceutically acceptable salt thereof, and at least one pharmaceutically acceptable diluent or carrier.

This specification also describes, in part, a compound of Formula (I), or a pharmaceutically acceptable salt thereof, for use in therapy.

This specification also describes, in part, a compound of Formula (I), or a pharmaceutically acceptable salt thereof, for use in the treatment of cancer.

This specification also describes, in part, use of a compound of Formula (I), or a pharmaceutically acceptable salt thereof, for the manufacture of a medicament for the treatment of cancer.

This specification also describes, in part, a method for treating cancer in a warm blooded animal in need of such treatment, which comprises administering to said warm-blooded animal a therapeutically effective amount of a compound of Formula (I), or a pharmaceutically acceptable salt thereof.

DESCRIPTION OF ILLUSTRATE EMBODIMENTS

Many embodiments are detailed throughout the specification and will be apparent to a reader skilled in the art. The invention is not to be interpreted as being limited to any particular embodiment(s) thereof.

In the first embodiment there is provided a compound of Formula (I):

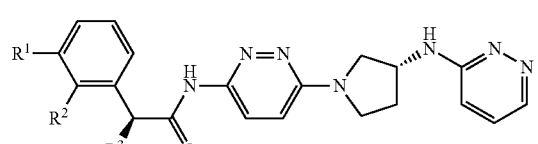

or a pharmaceutically acceptable salt thereof, where:
$R^1$ is hydro, methoxy, difluoromethoxy or trifluoromethoxy;
$R^2$ is hydro, methoxy, trifluoromethoxy or trifluoromethyl; and
$R^3$ is hydro or methoxy.

A hydro group is a single hydrogen atom. For example, where $R^3$ is hydro, the group adjacent to the carbonyl group in Formula (I) is a methylene group. Where $R^1$ or $R^2$ are hydro, they and the carbon atom to which they are attached form an aromatic CH group.

The term "pharmaceutically acceptable" is used to specify that an object (for example a salt, dosage form, diluent or carrier) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zurich: Wiley-VCH/VHCA, 2002. A suitable pharmaceutically acceptable salt of a compound of Formula (I) is, for example, an acid-addition salt. An acid addition salt of a compound of Formula (I) may be formed by bringing the compound into contact with a suitable inorganic or organic acid under conditions known to the skilled person. An acid addition salt may for example be formed using an inorganic acid selected from hydrochloric acid, hydrobromic acid, sulphuric acid, and phosphoric acid. An acid addition salt may also for example be formed using an organic acid selected from trifluoroacetic acid, methanesulfonic acid and benzenesulfonic acid.

Therefore, in one embodiment there is provided a compound of Formula (I) or a pharmaceutically acceptable salt thereof, where the pharmaceutically acceptable salt is a hydrochloric acid, hydrobromic acid, sulphuric acid, phosphoric acid, trifluoroacetic acid, methanesulfonic acid or benzenesulfonic acid salt.

In one embodiment there is provided a compound of Formula (I) or a pharmaceutically acceptable salt thereof, where the pharmaceutically acceptable salt is a hydrochloric acid or hydrobromic acid salt.

It is to be understood that it may be possible to form other pharmaceutically acceptable salts with other suitable acids of appropriate PKa, and these are included in the definition of "pharmaceutically acceptable salts".

A further suitable pharmaceutically acceptable salt of a compound of Formula (I) is a base-addition salt. A base addition salt of a compound of Formula (I) may be formed by bringing the compound into contact with a suitable inorganic or organic base under conditions known to the skilled person. A base addition salt may for example be formed using an inorganic base selected from an alkali metal hydroxide (such as sodium, potassium, or lithium hydroxide) or an alkaline earth metal hydroxide (such as calcium hydroxide or magnesium hydroxide). A base addition salt may also be formed using an organic base selected from methylamine, dimethylamine, trimethylamine, piperidine, morpholine and tris-(2-hydroxyethyl)amine.

Therefore, in one embodiment there is provided a compound of Formula (I) or a pharmaceutically acceptable salt thereof, where the pharmaceutically acceptable salt is a sodium hydroxide, potassium hydroxide, lithium hydroxide, calcium hydroxide, magnesium hydroxide, methylamine, dimethylamine, trimethylamine, piperidine, morpholine or tris-(2-hydroxyethyl)amine salt.

In one embodiment there is provided a compound of Formula (I) or a pharmaceutically acceptable salt thereof, where the pharmaceutically acceptable salt is a hydrochloric acid, hydrobromic acid, sulphuric acid, phosphoric acid, trifluoroacetic acid, methanesulfonic acid, benzenesulfonic acid, sodium hydroxide, potassium hydroxide, lithium hydroxide, calcium hydroxide, magnesium hydroxide, methylamine, dimethylamine, trimethylamine, piperidine, morpholine or tris-(2-hydroxyethyl)amine salt.

It is to be understood that it may be possible to form other pharmaceutically acceptable bases with other suitable bases, and these are included in the definition of "pharmaceutically acceptable salts".

A further embodiment provides any of the embodiments defined herein (for example the embodiment of claim 1) with the proviso that one or more specific Examples (for instance one, two or three specific Examples, or alternatively one specific Example) selected from Examples 1, 2, 3, 4, 5 and 6 is individually disclaimed.

Some values of variable groups in Formula (I) are as follows. Such values may be used in combination with any of the definitions, claims (for example claim 1), or embodiments defined herein to provide further embodiments.

a) $R^1$ is methoxy, difluoromethoxy or trifluoromethoxy.
b) $R^1$ is methoxy or difluoromethoxy.
c) $R^1$ is methoxy or trifluoromethoxy.
d) $R^1$ is difluoromethoxy or trifluoromethoxy.
e) $R^1$ is hydro.
f) $R^1$ is methoxy.
g) $R^1$ is difluoromethoxy.
h) $R^1$ is trifluoromethoxy.
i) $R^2$ is methoxy, trifluoromethoxy or trifluoromethyl.
j) $R^2$ is hydro.
k) $R^2$ is methoxy.
l) $R^2$ is trifluoromethoxy.
m) $R^2$ trifluoromethyl.
n) $R^3$ is hydro.
o) $R^3$ is methoxy.

In one embodiment, there is provided a compound of Formula (I), or a pharmaceutically acceptable salt thereof, where:
$R^1$ is hydro, methoxy, difluoromethoxy or trifluoromethoxy;
$R^2$ is hydro; and
$R^3$ is methoxy.

In one embodiment, there is provided a compound of Formula (I), or a pharmaceutically acceptable salt thereof, where:
$R^1$ is methoxy, difluoromethoxy or trifluoromethoxy;
$R^2$ is hydro; and
$R^3$ is methoxy.

In one embodiment, there is provided a compound of Formula (I), or a pharmaceutically acceptable salt thereof, where:
$R^1$ is hydro;
$R^2$ is methoxy, trifluoromethoxy or trifluoromethyl; and
$R^3$ is hydro.

In one embodiment there is provided a compound of Formula (I), or a pharmaceutically acceptable salt thereof, where the compound of Formula (I) is selected from:
(2S)-2-[3-(Difluoromethoxy)phenyl]-2-methoxy-N-[6-[(3R)-3-(pyridazin-3-ylamino)pyrrolidin-1-yl]pyridazin-3-yl]acetamide;
(2S)-2-[3-(Trifluoromethoxy)phenyl]-2-methoxy-N-[6-[(3R)-3-(pyridazin-3-ylamino)pyrrolidin-1-yl]pyridazin-3-yl]acetamide;
(2S)-2-Methoxy-2-(3-methoxyphenyl)-N-[6-[(3R)-3-(pyridazin-3-ylamino)pyrrolidin-1-yl]pyridazin-3-yl]acetamide;
2-(2-Methoxyphenyl)-N-[6-[(3R)-3-(pyridazin-3-ylamino)pyrrolidin-1-yl]pyridazin-3-yl]acetamide;
N-[6-[(3R)-3-(Pyridazin-3-ylamino)pyrrolidin-1-yl]pyridazin-3-yl]-2-[2-(trifluoromethyl)phenyl]acetamide; and
N-[6-[(3R)-3-(Pyridazin-3-ylamino)pyrrolidin-1-yl]pyridazin-3-yl]-2-[2-(trifluoromethoxy)phenyl]acetamide.

In one embodiment there is provided (2S)-2-[3-(difluoromethoxy)phenyl]-2-methoxy-N-[6-[(3R)-3-(pyridazin-3-ylamino)pyrrolidin-1-yl]pyridazin-3-yl]acetamide, or a pharmaceutically acceptable salt thereof.

In one embodiment there is provided (2S)-2-[3-(difluoromethoxy)phenyl]-2-methoxy-N-[6-[(3R)-3-(pyridazin-3-ylamino)pyrrolidin-1-yl]pyridazin-3-yl]acetamide.

In one embodiment there is provided a pharmaceutically acceptable salt of (2S)-2-[3-(difluoromethoxy)phenyl]-2-methoxy-N-[6-[(3R)-3-(pyridazin-3-ylamino)pyrrolidin-1-yl]pyridazin-3-yl]acetamide.

In one embodiment there is provided (2S)-2-[3-(trifluoromethoxy)phenyl]-2-methoxy-N-[6-[(3R)-3-(pyridazin-3-ylamino)pyrrolidin-1-yl]pyridazin-3-yl]acetamide, or a pharmaceutically acceptable salt thereof.

In one embodiment there is provided (2S)-2-[3-(trifluoromethoxy)phenyl]-2-methoxy-N-[6-[(3R)-3-(pyridazin-3-ylamino)pyrrolidin-1-yl]pyridazin-3-yl]acetamide.

In one embodiment there is provided a pharmaceutically acceptable salt of (2S)-2-[3-(trifluoromethoxy)phenyl]-2-methoxy-N-[6-[(3R)-3-(pyridazin-3-ylamino)pyrrolidin-1-yl]pyridazin-3-yl]acetamide.

In one embodiment there is provided (2S)-2-methoxy-2-(3-methoxyphenyl)-N-[6-[(3R)-3-(pyridazin-3-ylamino)pyrrolidin-1-yl]pyridazin-3-yl]acetamide, or a pharmaceutically acceptable salt thereof.

In one embodiment there is provided (2S)-2-methoxy-2-(3-methoxyphenyl)-N-[6-[(3R)-3-(pyridazin-3-ylamino)pyrrolidin-1-yl]pyridazin-3-yl]acetamide.

In one embodiment there is provided a pharmaceutically acceptable salt of (2S)-2-methoxy-2-(3-methoxyphenyl)-N-[6-[(3R)-3-(pyridazin-3-ylamino)pyrrolidin-1-yl]pyridazin-3-yl]acetamide.

In one embodiment there is provided 2-(2-Methoxyphenyl)-N-[6-[(3R)-3-(pyridazin-3-ylamino)pyrrolidin-1-yl]pyridazin-3-yl]acetamide, or a pharmaceutically acceptable salt thereof.

In one embodiment there is provided 2-(2-Methoxyphenyl)-N-[6-[(3R)-3-(pyridazin-3-ylamino)pyrrolidin-1-yl]pyridazin-3-yl]acetamide.

In one embodiment there is provided a pharmaceutically acceptable salt of 2-(2-Methoxyphenyl)-N-[6-[(3R)-3-(pyridazin-3-ylamino)pyrrolidin-1-yl]pyridazin-3-yl]acetamide.

Compounds and salts described in this specification may exist in solvated forms and unsolvated forms. For example, a solvated form may be a hydrated form, such as a hemi-hydrate, a mono-hydrate, a di-hydrate, a tri-hydrate or an alternative quantity thereof. The present invention encompasses all such solvated and unsolvated forms of compounds of Formula (I).

Atoms of the compounds and salts described in this specification may exist as their isotopes. The present invention encompasses all compounds of Formula (I) where an atom is replaced by one or more of its isotopes (for example a compound of Formula (I) where one or more carbon atom is an $^{11}$C or $^{13}$C carbon isotope, or where one or more hydrogen atoms is a $^{2}$H (deuterium) or $^{3}$H (tritium) isotope).

Compounds and salts described in this specification may exist as a mixture of tautomers. "Tautomers" are structural isomers that exist in equilibrium resulting from the migration of a hydrogen atom. The present invention includes all tautomers of compounds of Formula (I).

Compounds of Formula (I) exist in optically active forms by virtue of their asymmetric carbon atoms.

Certain compounds of formula (I) (for example those where $R^3$ is hydrogen) exist as a single enantiomer. Therefore, in one embodiment there is provided a compound of Formula (I), or a pharmaceutically acceptable salt thereof, which is a single enantiomer being in an enantiomeric excess (% ee) of ≥95%, ≥98% or ≥99%. In one embodiment, the single enantiomer is present in enantiomeric excess (% ee) of ≥99%.

Certain compounds of formula (I) (for example those where $R^3$ is methoxy) exist as a single diastereomer. Therefore, in one embodiment there is provided a compound of Formula (I), or a pharmaceutically acceptable salt thereof, which is a single diastereomer being in an diastereomeric excess (% de) of ≥95%, ≥98% or ≥99%. In one embodiment, the single diasteromer is present in a diasteromeric excess (% de) of ≥99%.

Compounds of Formula (I) may for example be prepared by the reaction of a compound of Formula (II):

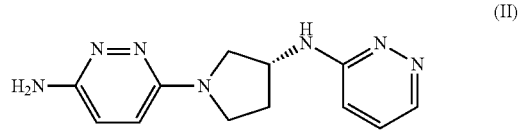 [SMILES: Nc1ccc(N2CC[C@@H](Nc3cccnn3)C2)nn1]

with a compound of formula (III):

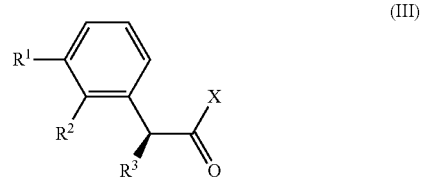

where $R^1$, $R^2$ and $R^3$ are as defined in any of the embodiments herein and X is a leaving group such as a halogen atom (for example a chlorine atom) or a hydroxy group. The reaction is conveniently performed in a suitable solvent (for example DMF or DMA) and in the presence of a base (for example DIPEA) at a suitable temperature (for example at ambient temperature of around 20 to 30° C. or at elevated temperature, such as between 80 and 120° C., or alternatively at around 100° C.). Where X is a hydroxy group, a suitable coupling agent (for example HATU) is used to form the amide bond.

Compounds of Formula (II), and salts thereof, are therefore useful as intermediates in the preparation of the compounds of Formula (I) and provide a further embodiment.

In one embodiment there is provided 6-[(3R)-3-(pyridazin-3-ylamino)pyrrolidin-1-yl]pyridazin-3-amine, or a salt thereof.

In one embodiment there is provided 6-[(3R)-3-(pyridazin-3-ylamino)pyrrolidin-1-yl]pyridazin-3-amine.

Compounds of Formula (III), and salts thereof, are similarly useful as intermediates in the preparation of the compounds of Formula (I) and provide a further embodiment.

In one embodiment there is provided a compound of Formula (III), or a salt thereof, where:
$R^1$ is difluoromethoxy or trifluoromethoxy;
$R^2$ is hydro;
$R^3$ is methoxy; and
X is a leaving group. In one embodiment X is hydroxy or chloro. In one embodiment X is hydroxy.

In one embodiment there is provided 2-[3-(difluoromethoxy)phenyl]-2-methoxyacetic acid, or a salt thereof.

In one embodiment there is provided 2-methoxy-2-[3-(trifluoromethoxy)phenyl]acetic acid, or a salt thereof.

In one embodiment there is provided 2-[3-(difluoromethoxy)phenyl]-2-methoxyacetic acid.

In one embodiment there is provided 2-methoxy-2-[3-(trifluoromethoxy)phenyl]acetic acid.

Compounds of formula (II) and formula (III) can be prepared by methods similar to those shown in the Example section.

A suitable salt of a compound of Formula (II) is, for example, an acid-addition salt. An acid addition salt of a compound of Formula (II) may be formed by bringing the compound into contact with a suitable inorganic or organic acid under conditions known to the skilled person. Such acids need not generate pharmaceutically acceptable salts when paired with a compound of Formula (II). An acid addition salt may for example be formed using an inorganic acid selected from hydrochloric acid, hydrobromic acid, sulphuric acid, and phosphoric acid. An acid addition salt may also for example be formed using an organic acid selected from trifluoroacetic acid, methanesulfonic acid and benzenesulfonic acid.

Therefore, in one embodiment there is provided a compound of Formula (II) or a salt thereof, where the salt is a hydrochloric acid, hydrobromic acid, sulphuric acid, phosphoric acid, trifluoroacetic acid, methanesulfonic acid or benzenesulfonic acid salt.

A suitable salt of a compound of Formula (III) is a base-addition salt. A base addition salt of a compound of Formula (III) may be formed by bringing the compound into contact with a suitable inorganic or organic base under conditions known to the skilled person. Such bases need not generate pharmaceutically acceptable salts when paired with a compound of Formula (III). A base addition salt may for example be formed using an inorganic base selected from an alkali metal hydroxide (such as sodium, potassium, or lithium hydroxide) or an alkaline earth metal hydroxide (such as calcium hydroxide or magnesium hydroxide). A base addition salt may also be formed using an organic base selected from methylamine, dimethylamine, trimethylamine, piperidine, morpholine and tris-(2-hydroxyethyl)amine.

Therefore, in one embodiment there is provided a compound of Formula (III) or a salt thereof, where the salt is a sodium hydroxide, potassium hydroxide, lithium hydroxide, calcium hydroxide, magnesium hydroxide, methylamine, dimethylamine, trimethylamine, piperidine, morpholine or tris-(2-hydroxyethyl)amine salt.

As a result of their GLS1 inhibitory activity, the compounds of Formula (I), and pharmaceutically acceptable salts thereof are expected to be useful in therapy, for example in the treatment of diseases or medical conditions mediated at least in part by GLS1, including cancer.

Where "cancer" is mentioned, this includes both non-metastatic cancer and also metastatic cancer, such that treating cancer involves treatment of both primary tumours and also tumour metastases.

In one embodiment the cancer is metastatic cancer.

In one embodiment the cancer is non-metastatic cancer.

"GLS1 inhibitory activity" refers to a decrease in the activity of GLS1 as a direct or indirect response to the presence of a compound of Formula (I), or pharmaceutically acceptable salt thereof, relative to the activity of GLS1 in the absence of compound of Formula (I), or pharmaceutically acceptable salt thereof. Such a decrease in activity may be due to the direct interaction of the compound of Formula (I), or pharmaceutically acceptable salt thereof with GLS1, or due to the interaction of the compound of Formula (I), or pharmaceutically acceptable salt thereof with one or more other factors that in turn affect GLS1 activity. For example, the compound of Formula (I), or pharmaceutically acceptable salt thereof may decrease GLS1 by directly binding to GLS1, by causing (directly or indirectly) another factor to decrease GLS1 activity, or by (directly or indirectly) decreasing the amount of GLS1 present in the cell or organism.

The term "therapy" is intended to have its normal meaning of dealing with a disease in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment" is used synonymously with "therapy". Similarly the term "treat" can be regarded as applying therapy where "therapy" is as defined herein.

In one embodiment there is provided a compound of Formula (I), or a pharmaceutically acceptable salt thereof, for use in therapy.

In one embodiment there is provided the use of the compound of Formula (I), or a pharmaceutically acceptable salt thereof, for the manufacture of a medicament.

In any embodiment the compound of Formula (I) is selected from the Examples. In any embodiment the compound of Formula (I) is selected from Examples 1, 2, 3, 4, 5 and 6.

In one embodiment there is provided a compound of Formula (I), or a pharmaceutically acceptable salt thereof, for use in the treatment of a disease mediated by GLS1. In one embodiment, said disease mediated by GLS1 is cancer. In one embodiment, said cancer is selected from breast cancer (for example triple negative breast cancer), lung cancer (for example non-small cell lung cancer), pancreatic cancer and hepatocellular cancer.

"Triple negative breast cancer" is any breast cancer that does not express the genes for the oestrogen receptor, progesterone receptor and Her2/neu.

In one embodiment there is provided a compound of Formula (I), or a pharmaceutically acceptable salt thereof, for use in the treatment of cancer. In one embodiment there is provided the use of the compound of Formula (I), or a pharmaceutically acceptable salt thereof, for the manufacture of a medicament for the treatment of a disease mediated by GLS1. In one embodiment, said disease mediated by GLS1 is cancer. In one embodiment, said cancer is selected from breast cancer (for example triple negative breast cancer), lung cancer (for example non-small cell lung cancer), pancreatic cancer and hepatocellular cancer.

In one embodiment there is provided the use of the compound of Formula (I), or a pharmaceutically acceptable salt thereof, for the manufacture of a medicament for the treatment of cancer.

In any embodiment the compound of Formula (I) is selected from the Examples. In any embodiment the compound of Formula (I) is selected from Examples 1, 2, 3, 4, 5 and 6.

In one embodiment there is provided a method for treating a disease in which inhibition of GLS1 is beneficial in a warm-blooded animal in need of such treatment, which comprises administering to said warm-blooded animal a therapeutically effective amount of a compound of Formula (I), or a pharmaceutically acceptable salt thereof.

The term "therapeutically effective amount" refers to an amount of a compound of Formula (I) as described in any of the embodiments herein which is effective to provide "therapy" in a subject, or to "treat" a disease or disorder in a subject. In the case of cancer, the therapeutically effective amount may cause any of the changes observable or measurable in a subject as described in the definition of "therapy", "treatment" and "prophylaxis" above. For example, the effective amount can reduce the number of cancer or tumor cells; reduce the overall tumor size; inhibit or stop tumor cell infiltration into peripheral organs including, for example, the soft tissue and bone; inhibit and stop tumor metastasis; inhibit and stop tumor growth; relieve to some extent one or more of the symptoms associated with the cancer; reduce morbidity and mortality; improve quality of life; or a combination of such effects. An effective amount may be an amount sufficient to decrease the symptoms of a disease responsive to inhibition of GLS1 activity. For cancer therapy, efficacy in-vivo can, for example, be measured by assessing the duration of survival, time to disease progression (TTP), the response rates (RR), duration of response, and/or quality of life. As recognized by those skilled in the art, effective amounts may vary depending on route of administration, excipient usage, and co-usage with other agents. For example, where a combination therapy is used, the amount of the compound of formula (I) or pharmaceutcially acceptable salt described in this specification and the amount of the other pharmaceutically active agent(s) are, when combined, jointly effective to treat a targeted disorder in the animal patient. In this context, the combined amounts are in a "therapeutically effective amount" if they are, when combined, sufficient to decrease the symptoms of a disease responsive to inhibition of GLS1 activity as described above. Typically, such amounts may be determined by one skilled in the art by, for example, starting with the dosage range described in this specification for the compound of formula (I) or pharmaceutcially acceptable salt thereof and an approved or otherwise published dosage range(s) of the other pharmaceutically active compound(s).

"Warm-blooded animals" include, for example, humans.

In one embodiment there is provided a method for treating cancer in a warm-blooded animal in need of such treatment, which comprises administering to said warm-blooded animal a therapeutically effective amount of a compound of Formula (I), or a pharmaceutically acceptable salt thereof. In one embodiment, said cancer is selected from breast cancer (for example triple negative breast cancer), lung cancer (for example non-small cell lung cancer), pancreatic cancer and hepatocellular cancer.

In any embodiment the compound of Formula (I) is selected from the Examples. In any embodiment the compound of Formula (I) is selected from Examples 1, 2, 3, 4, 5 and 6.

The anti-cancer treatment described in this specification may be applied as a sole therapy, or may involve, in addition to administration of the compound of Formula (I), conventional surgery, radiotherapy or chemotherapy; or a combination of such additional therapies. Such conventional surgery, radiotherapy or chemotherapy may be administered simultaneously, sequentially or separately to treatment with the compound of Formula (I).

Therefore, in one embodiment there is provided a compound of Formula (I), or a pharmaceutically acceptable salt thereof, and at least one additional anti-tumour substance, for use in the treatment of cancer.

In one embodiment there is provided a compound of Formula (I), or a pharmaceutically acceptable salt thereof, and at least one additional anti-tumour substance for use in the simultaneous, separate or sequential treatment of cancer.

In one embodiment there is provided a compound of Formula (I), or a pharmaceutically acceptable salt thereof, for use in the treatment of cancer, where the compound of Formula (I) is administered simultaneously, separately or sequentially with at least one additional anti-tumour substance.

In one embodiment there is provided a method of treating cancer in a warm-blooded animal who is in need of such treatment, which comprises administering to said warm-blooded animal a compound of Formula (I), or a pharmaceutically acceptable salt thereof and at least one additional anti-tumour substance, wherein the amounts of the compound of Formula (I), or a pharmaceutically acceptable salt thereof, and the additional anti-tumour substance are jointly effective in producing an anti-cancer effect.

In one embodiment there is provided a method of treating cancer in a warm-blooded animal who is in need of such treatment, which comprises administering to said warm-blooded animal a compound of Formula (I), or a pharmaceutically acceptable salt thereof, and simultaneously, separately or sequentially administering at least one additional anti-tumour substance to said warm-blooded animal, wherein the amounts of the compound of Formula (I), or pharmaceutically acceptable salt thereof, and the additional anti-tumour substance are jointly effective in producing an anti-cancer effect.

In any embodiment the additional anti-tumour substance is a taxane. In one embodiment the taxane is paclitaxel. In one embodiment the taxane is docetaxel.

In any embodiment the additional anti-tumour substance is a platinum therapy. In one embodiment the platinum therapy is cis-platin, oxaliplatin, or carboplatin.

In one embodiment there is provided a pharmaceutical composition comprising a compound of Formula (I) and at least one additional anti-tumour substance. In one embodiment the pharmaceutical composition also comprises at least one pharmaceutically acceptable diluent or carrier.

In one embodiment there is provided a pharmaceutical composition comprising a compound of Formula (I) and at least one additional anti-tumour substance, for use in the treatment of cancer. In one embodiment the pharmaceutical composition also comprises at least one pharmaceutically acceptable diluent or carrier.

In one embodiment the additional anti-tumour substance is a taxane. In one embodiment the taxane is paclitaxel. In one embodiment the taxane is docetaxel.

In one embodiment the additional anti-tumour substance is a platinum therapy. In one embodiment the platinum therapy is cis-platin, oxaliplatin, or carboplatin.

In any embodiment the compound of Formula (I) is selected from the Examples. In any embodiment the compound of Formula (I) is selected from Examples 1, 2, 3, 4, 5 and 6.

According to a further embodiment there is provided a kit comprising:

a) A compound of formula (I), or a pharmaceutically acceptable salt thereof, in a first unit dosage form;

b) A further additional anti-tumour substance in a further unit dosage form;

c) Container means for containing said first and further unit dosage forms; and
   optionally
d) Instructions for use.

In one embodiment the additional anti-tumour substance is a taxane. In one embodiment the taxane is paclitaxel. In one embodiment the taxane is docetaxel.

In one embodiment the additional anti-tumour substance is a platinum therapy. In one embodiment the platinum therapy is cis-platin, oxaliplatin, or carboplatin.

In one embodiment the compound of Formula (I) is selected from the Examples. In one embodiment the compound of Formula (I) is selected from Examples 1, 2, 3, 4, 5 and 6.

The compounds of Formula (I), and pharmaceutically acceptable salts thereof, may be administered as pharmaceutical compositions, comprising one or more pharmaceutically acceptable diluents or carriers.

Therefore, in one embodiment there is provided a pharmaceutical composition comprising a compound of Formula (I), or a pharmaceutically acceptable salt thereof, and at least one pharmaceutically acceptable diluent or carrier.

In one embodiment the compound of Formula (I) is selected from the Examples. In one embodiment the compound of Formula (I) is selected from Examples 1, 2, 3, 4, 5 and 6.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing), or as a suppository for rectal dosing. The compositions of the invention may be obtained by conventional procedures using conventional pharmaceutical excipients, well known in the art. Thus, compositions intended for oral use may contain, for example, one or more colouring, sweetening, flavouring and/or preservative agents.

In one embodiment there is provided a pharmaceutical composition comprising a compound of Formula (I), or a pharmaceutically acceptable salt thereof, and at least one pharmaceutically acceptable diluent or carrier, for use in therapy.

In one embodiment there is provided a pharmaceutical composition comprising a compound of Formula (I), or a pharmaceutically acceptable salt thereof, and at least one pharmaceutically acceptable diluent or carrier, for use in the treatment of cancer. In one embodiment said cancer is selected from breast cancer (for example triple negative breast cancer), lung cancer (for example non-small cell lung cancer), pancreatic cancer and hepatocellular cancer.

In any embodiment the compound of Formula (I) is selected from the Examples. In any embodiment the compound of Formula (I) is selected from Examples 1, 2, 3, 4, 5 and 6.

The compound of Formula (I) will normally be administered to a warm-blooded animal at a unit dose within the range 5-5000 mg/m$^2$ body area of the animal, or for example approximately 0.1-100 mg/kg, and this normally provides a therapeutically effective dose. A unit dose form such as a tablet or capsule will usually contain, for example 1-250 mg of active ingredient. The daily dose will necessarily be varied depending upon the host treated, the particular route of administration, any therapies being co-administered, and the severity of the illness being treated. Accordingly the practitioner who is treating any particular patient may determine the optimum dosage.

EXAMPLES

The various embodiments are illustrated by the following Examples. The invention is not to be interpreted as being limited to the Examples. During the preparation of the Examples, generally:

i. Operations were carried out at ambient temperature, i.e. in the range of about 17 to 30° C. and under an atmosphere of an inert gas such as nitrogen unless otherwise stated;

ii. Evaporations were carried out by rotary evaporation or utilising Genevac equipment in vacuo and work-up procedures were carried out after removal of residual solids by filtration;

iii. Flash chromatography purifications were performed on an automated Isco Combiflash Companion using Grace Resolve prepacked silica columns, and (reverse phase flash) Isco Combiflash Rf using Redisep Gold C18 columns;

iv. Yields, where present, are not necessarily the maximum attainable;

v. Structures of end-products of Formula (I) were confirmed by nuclear magnetic resonance (NMR) spectroscopy, with NMR chemical shift values measured on the delta scale. Proton magnetic resonance spectra were determined using a Bruker advance 700 (700 MHz), Bruker Avance 500 (500 MHz), Bruker 400 (400 MHz) or Bruker 300 (300 MHz) instrument; 19F NMR were determined at 282 MHz or 376 MHz; 13C NMR were determined at 75 MHz or 100 MHz; measurements were taken at around 20-30° C. unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal;

vi. End-products of Formula (I) were also characterised by mass spectroscopy following liquid chromatography (LCMS), using a HPLC system based on a Waters 2790/95 LC system with a 2996 PDA and a 2000 amu ZQ single quadrupole mass spectrometer. The solvents used were A=Water, B=Acetonitrile, C=50:50 acetonitrile:water 0.1% formic acid and D=50:50 acetonitrile:water 0.1% ammonium hydroxide. At a flow rate of 1.1 mL/min 5 μL of sample was injected onto a 50×2.1 5 μm Phenomenex Gemini NX column. The gradient ran from 95% A to 95% B for 4.0 mins with a constant 5% infusion of C (for acid analysis, D is used for base analysis). The flow was held at 95% B for 0.5 mins before returning to start conditions. The Data was acquired from 150 to 850 amu in both positive and negative mode on the Mass Spectrometer and 220-320 nm on the PDA. LCMS was also performed on a UPLC system utilising a Waters Aquity Binary pump with sample manager, Aquity PDA and an SQD Mass spectrometer. The solvents used were A1=0.1% formic acid (aq), B1 0.1% formic acid in acetonitrile, A2=0.1% ammonium hydroxide (aq) and B2 0.1% ammonium hydroxide in acetonitrile. At a flow rate of 1 mL/min 1 uL of sample was injected onto a 50×2.1 1.7 μm Waters BEH column (at 40° C.). The gradient ran from 97% A1 to 97% B1 over 1.30 mins before being held for 0.2 min and returning to start conditions (substitute A1 and B1 for A2 and B2 for base analysis). Data was acquired from 150-1000 amu in positive and negative ion mode on the mass spectrometer and 245-320 amu on the PDA;

vii. Intermediates were not generally fully characterised and purity was assessed by thin layer chromatographic, mass spectral, HPLC and/or NMR analysis;

viii. The following abbreviations have been used: h=hour(s); r.t.=room temperature (~17-30° C.); conc.=concentrated; FCC=flash column chromatography using silica; DCM=dichloromethane; DIPEA=diisopropyl ethylamine; DMA=N,N-dimethylacetamide; DMF=N,N-dimethylformamide; DMSO=dimethylsulfoxide; Et$_2$O=diethyl ether; EtOAc=ethyl acetate; EtOH=ethanol; HATU=1-[bis(dimethylamino)methylene]-1H-1,2,3-triazolo[4,5-b]pyridinium 3-oxid hexafluorophosphate; K$_2$CO$_3$=potassium carbonate; MeOH=methanol; MeCN=acetonitrile; MgSO$_4$=anhydrous magnesium sulphate; Na$_2$SO$_4$=anhydrous sodium sulphate; TFA=trifluoroacetic acid; THF=tetrahydrofuran; sat.=saturated aqueous solution; and ix. IUPAC names were generated using 'SmiToSd', a proprietary program built around the OpenEye Lexichem toolkit (http://www.eyesopen.com/lexichem-tk).

Example 1

(2S)-2-[3-(Difluoromethoxy)phenyl]-2-methoxy-N-[6-[(3R)-3-(pyridazin-3-ylamino)pyrrolidin-1-yl]pyridazin-3-yl]acetamide

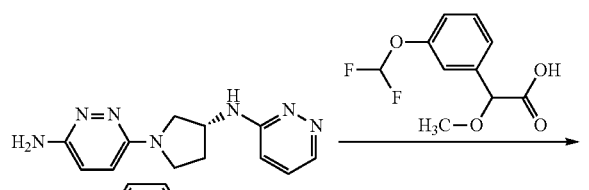

Example 1

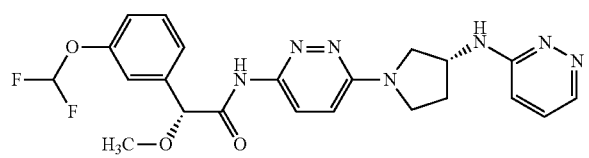

Byproduct 1

HATU (931 mg, 2.45 mmol) was added to 6-[(3R)-3-(pyridazin-3-ylamino)pyrrolidin-1-yl]pyridazin-3-amine (Intermediate 1, 525 mg, 2.04 mmol), 2-(3-(difluoromethoxy)phenyl)-2-methoxyacetic acid (Intermediate 6, 521 mg, 2.24 mmol) and DIPEA (1.066 mL, 6.12 mmol) in DMF (12 mL). The resulting solution was stirred at 0° C. for 5 minutes and then at r.t. for 3 h. This solution was diluted with MeOH (7 mL) and passed through a 20 g SCX-2 cartridge, flushing with MeOH to remove impurities, followed by a 1N solution of ammonia in MeOH to bring off the product. The solvent was evaporated under reduced pressure to yield crude product. The residue was purified by FCC, elution gradient 0 to 6% MeOH in DCM. Fractions containing product were evaporated to dryness to afford 2-(3-(difluoromethoxy)phenyl)-2-methoxy-N-(6-((R)-3-(pyridazin-3-ylamino)pyrrolidin-1-yl)pyridazin-3-yl)acetamide (490 mg, 50%) as a solid. The crude product was purified by preparative HPLC (Chiralpak IF column, 20 μm silica, 50 mm diameter, 250 mm length), eluting with MeOH 100% at 150 mL/min. Fractions containing the desired compounds were evaporated to dryness to afford:

(2S)-2-[3-(Difluoromethoxy)phenyl]-2-methoxy-N-[6-[(3R)-3-(pyridazin-3-ylamino)pyrrolidin-1-yl]pyridazin-3-yl]acetamide (Example 1) as the first eluted isomer (169 mg, 18%).

$^1$H NMR (400 MHz, DMSO, 30° C.) δ 2.0-2.1 (1H, m), 2.29-2.39 (1H, m), 3.37 (3H, s), 3.39-3.45 (1H, m), 3.51-3.66 (2H, m), 3.83 (1H, dd), 4.58-4.67 (1H, m), 5.02 (1H, s), 6.81 (1H, dd), 6.98 (1H, d), 7.04-7.48 (7H, m), 7.91 (1H, d), 8.46 (1H, dd), 10.58 (1H, s); m/z: ES$^+$ [M+H]$^+$ 472.

(2R)-2-[3-(Difluoromethoxy)phenyl]-2-methoxy-N-[6-[(3R)-3-(pyridazin-3-ylamino)pyrrolidin-1-yl]pyridazin-3-yl]acetamide (Byproduct 1) as the second eluted isomer (178 mg, 19%).

$^1$H NMR (400 MHz, DMSO, 30° C.) δ 2.04-2.15 (1H, m), 2.32-2.44 (1H, m), 3.41 (3H, s), 3.46 (1H, dd), 3.55-3.71 (2H, m), 3.87 (1H, dd), 4.62-4.72 (1H, m), 5.07 (1H, s), 6.86 (1H, d), 7.02 (1H, d), 7.09-7.53 (7H, m), 7.95 (1H, d), 8.50 (1H, d), 10.65 (1H, s); m/z: ES$^+$ [M+H]$^+$ 472.

Example 2

(2S)-2-[3-(Trifluoromethoxy)phenyl]-2-methoxy-N-[6-[(3R)-3-(pyridazin-3-ylamino)pyrrolidin-1-yl]pyridazin-3-yl]acetamide

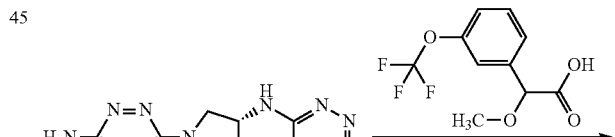

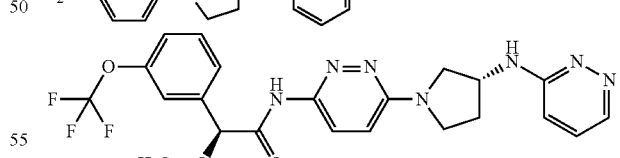

Example 2

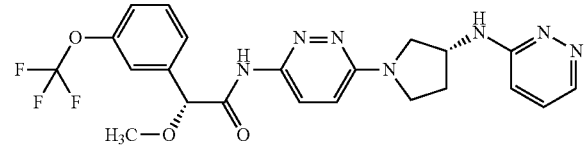

Byproduct 2

HATU (355 mg, 0.93 mmol) was added to 2-methoxy-2-(3-(trifluoromethoxy)phenyl)acetic acid (Intermediate 7, 214 mg, 0.86 mmol), 6-[(3R)-3-(pyridazin-3-ylamino)pyrrolidin-1-yl]pyridazin-3-amine (Intermediate 1, 200 mg, 0.78 mmol), and DIPEA (0.406 mL, 2.33 mmol) in DMF (4 mL) at 21° C. The resulting solution was then stirred at ambient temperature for 1 h. The crude product was purified by ion exchange chromatography, using an SCX column. The crude product was eluted from the column using 1M ammonia/MeOH and adsorbed onto silica. The crude product was purified by FCC, elution gradient 0 to 7% MeOH (with 7M ammonia/MeOH) in DCM. Pure fractions were evaporated to dryness to afford the mixture of diastereoisomers as a gum (150 mg). The mixture was then separated using preparative chiral HPLC (20 μm silica, 50 mm diameter, 250 mm length) using MeOH as eluent. Fractions containing the desired compounds were evaporated to dryness to afford:

(2R)-2-[3-(Trifluoromethoxy)phenyl]-2-methoxy-N-[6-[(3R)-3-(pyridazin-3-ylamino)pyrrolidin-1-yl]pyridazin-3-yl]acetamide (Byproduct 2) as the first eluted isomer (47.0 mg, 12%).

$^1$H NMR (400 MHz, DMSO, 30° C.) δ 2-2.14 (1H, m), 2.26-2.43 (1H, m), 3.38 (3H, s), 3.42 (1H, m), 3.51-3.66 (2H, m), 3.83 (1H, m), 4.53-4.71 (1H, m), 5.07 (1H, s), 6.81 (1H, dd), 6.97 (1H, d), 7.08 (1H, d), 7.24 (1H, dd), 7.3-7.4 (1H, m), 7.48 (1H, s), 7.52-7.59 (2H, m), 7.90 (1H, d), 8.45 (1H, dd), 10.63 (1H, s); m/z: ES$^+$ [M+H]$^+$ 490.

(2S)-2-[3-(Trifluoromethoxy)phenyl]-2-methoxy-N-[6-[(3R)-3-(pyridazin-3-ylamino)pyrrolidin-1-yl]pyridazin-3-yl]acetamide (Example 2) as the second eluted isomer (178 mg, 19%).

$^1$H NMR (400 MHz, DMSO, 30° C.) δ 2-2.14 (1H, m), 2.26-2.43 (1H, m), 3.38 (3H, s), 3.42 (1H, m), 3.51-3.66 (2H, m), 3.83 (1H, m), 4.53-4.71 (1H, m), 5.07 (1H, s), 6.81 (1H, dd), 6.97 (1H, d), 7.08 (1H, d), 7.24 (1H, dd), 7.3-7.4 (1H, m), 7.48 (1H, s), 7.52-7.59 (2H, m), 7.90 (1H, d), 8.45 (1H, dd), 10.63 (1H, s); m/z: ES$^+$ [M+H]$^+$ 490.

Example 3

(2S)-2-Methoxy-2-(3-methoxyphenyl)-N-[6-[(3R)-3-(pyridazin-3-ylamino)pyrrolidin-1-yl]pyridazin-3-yl]acetamide

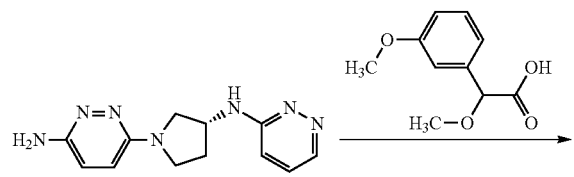

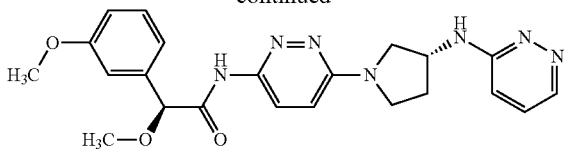

Example 3

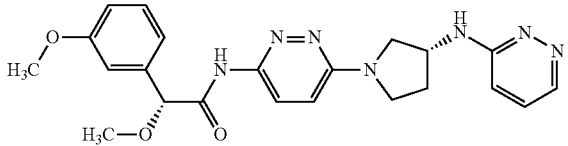

Byproduct 3

HATU (355 mg, 0.93 mmol) was added to 2-methoxy-2-(3-methoxyphenyl)acetic acid (Intermediate 8, 168 mg, 0.86 mmol), 6-[(3R)-3-(pyridazin-3-ylamino)pyrrolidin-1-yl]pyridazin-3-amine (Intermediate 1, 200 mg, 0.78 mmol), and DIPEA (0.406 mL, 2.33 mmol) in DMF (4 mL) at 21° C. The resulting solution was then stirred at ambient temperature for 1 h. The crude product was purified by ion exchange chromatography, using an SCX column. The desired product was eluted from the column using 1M ammonia/MeOH and pure fractions were adsorbed onto silica. The crude product was purified by FCC, elution gradient 0 to 7% MeOH (with 7M ammonia/MeOH) in DCM. Pure fractions were evaporated to dryness to afford a mixture of diastereoisomers as a solid. The crude product was purified by chiral preparative HPLC (Phenomonex Lux C2 column, 20 μm silica, 50 mm diameter, 250 mm length), EtOH/MeOH 50/50 at 100 mL/min. Fractions containing the desired compounds were evaporated to dryness to afford:

(2S)-2-Methoxy-2-(3-methoxyphenyl)-N-[6-[(3R)-3-(pyridazin-3-ylamino)pyrrolidin-1-yl]pyridazin-3-yl]acetamide (Example 3) as the first eluted isomer (80 mg, 24%).

$^1$H NMR (500 MHz, DMSO, 30° C.) δ 1.95-2.16 (1H, m), 2.21-2.42 (1H, m), 3.35 (3H, s), 3.42 (1H, m), 3.52-3.68 (2H, m), 3.76 (3H, s), 3.82 (1H, m), 4.55-4.7 (1H, m), 4.95 (1H, s), 6.82 (1H, d), 6.86-6.93 (1H, d), 6.98 (1H, d), 7.04-7.15 (3H, m), 7.25 (1H, dd), 7.28-7.32 (1H, dd), 7.91 (1H, d), 8.46 (1H, dd), 10.47 (1H, s); m/z: ES$^+$ [M+H]$^+$ 436.

(2R)-2-Methoxy-2-(3-methoxyphenyl)-N-[6-[(3R)-3-(pyridazin-3-ylamino)pyrrolidin-1-yl]pyridazin-3-yl]acetamide (Byproduct 3) as the second eluted isomer (75 mg, 22%).

$^1$H NMR (500 MHz, DMSO, 30° C.) δ 1.95-2.16 (1H, m), 2.21-2.42 (1H, m), 3.35 (3H, s), 3.42 (1H, m), 3.52-3.68 (2H, m), 3.76 (3H, s), 3.82 (1H, m), 4.55-4.7 (1H, m), 4.95 (1H, s), 6.82 (1H, d), 6.86-6.93 (1H, d), 6.98 (1H, d), 7.04-7.15 (3H, m), 7.25 (1H, dd), 7.28-7.32 (1H, dd), 7.91 (1H, d), 8.46 (1H, dd), 10.47 (1H, s); m/z: ES$^+$ [M+H]$^+$ 436.

Example 4

2-(2-Methoxyphenyl)-N-[6-[(3R)-3-(pyridazin-3-ylamino)pyrrolidin-1-yl]pyridazin-3-yl]acetamide

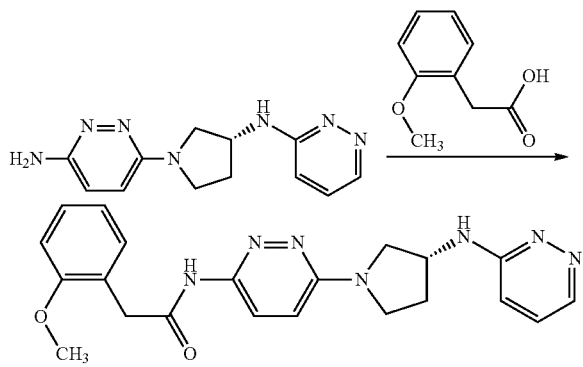

6-[(3R)-3-(Pyridazin-3-ylamino)pyrrolidin-1-yl] pyridazin-3-amine (Intermediate 1, 0.03 g, 0.117 mmol) and (2-methoxyphenyl)acetic acid (0.02 g, 0.117 mmol) were dissolved in DMF (1 mL). Subsequently, HATU (0.04 g, 0.117 mmol) was added and the reaction stirred for 5 mins. DIPEA (0.04 g, 0.291 mmol) was then added in one portion and the mixture was allowed to stir at r.t. for 15 h. The solvent was removed under reduced pressure and crude product was absorbed onto silica and purified by FCC with a solvent gradient from 100% DCM to 10% MeOH 90% DCM. Fractions were combined and concentrated under reduced pressure to afford a colourless gum (30 mg). LCMS of this material showed that it was impure, hence the solid was dissolved in DMSO and purified by preparative HPLC (Waters C18 SunFire column, 5 μm pore size, 4.60 mm diameter, 50 mm length) using decreasingly polar mixtures of water (containing 0.1% of formic acid) and acetonitrile (containing 0.1% of formic acid) as eluents. Fractions containing the desired compound were evaporated to dryness, dissolved in MeOH and passed through an SCX column, flushing with MeOH and then eluting the product with 2M ammonia in MeOH. Solvent was evaporated under reduced pressure to afford 2-(2-methoxyphenyl)-N-[6-[(3R)-3-(pyridazin-3-ylamino)pyrrolidin-1-yl]pyridazin-3-yl]acetamide (17 mg, 47%) as a cream coloured solid. $^1$H NMR (400 MHz, DMSO, 21.8° C.) δ 2.04-2.12 (1H, m), 2.32-2.41 (1H, m), 3.44-3.47 (m, 1H), 3.56-3.68 (m, 2H), 3.73 (s, 2H), 3.79 (s, 3H), 3.85 (dd, 1H), 4.62-4.69 (m, 1H), 6.85 (dd, 1H), 6.93 (td, 1H), 7.01 (d, 2H), 7.17 (d, 1H), 7.23 7.30 (m, 3H), 8.01 (d, 1H), 8.49 (dd, 1H), 10.65 (s, 1H); m/z: ES$^+$ [M+H]$^+$ 406.3.

Example 5

N-[6-[(3R)-3-(Pyridazin-3-ylamino)pyrrolidin-1-yl]pyridazin-3-yl]-2-[2-(trifluoromethyl)phenyl]acetamide

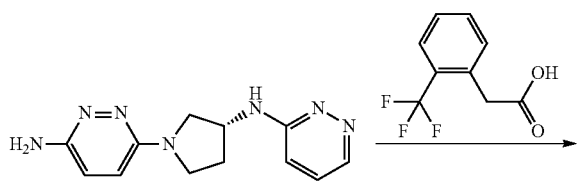

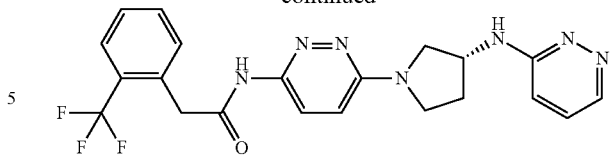

To a stirred mixture of 6-[(3R)-3-(pyridazin-3-ylamino)pyrrolidin-1-yl]pyridazin-3-amine (Intermediate 1, 0.041 g, 0.159 mmol), 2-[2-(trifluoromethyl)phenyl]acetic acid (0.032 g, 0.159 mmol) and HATU (0.061 g, 0.159 mmol) in dry DMF (1 mL) was added DIPEA (0.052 g, 0.398 mmol) and the mixture was left to stir under a nitrogen atmosphere for 15 h. The solvent was removed by evaporation under reduced pressure to give a brown gum which was dissolved in DMSO and purified by preparative HPLC (Waters C18 SunFire column, 5 μm pore size, 4.60 mm diameter, 50 mm length) using decreasingly polar mixtures of water (containing 0.1% of formic acid) and acetonitrile (containing 0.1% of formic acid) as eluents. Fractions containing the desired compound were evaporated to dryness to give N-[6-[(3R)-3-(pyridazin-3-ylamino)pyrrolidin-1-yl]pyridazin-3-yl]-2-[2-(trifluoromethyl)phenyl]acetamide as a colourless powder (0.065 g, 41%).
$^1$H NMR (400 MHz, DMSO, 21.8° C.) δ 2.07-2.12 (1H, m), 2.30-2.38 (1H, m), 3.48-3.51 (m, 1H), 3.55-3.66 (m, 2H), 3.83 (dd, 1H), 4.00 (s, 2H), 4.59-4.61 (m, 1H), 7.01 (d, 1H), 7.11 (d, 1H), 7.43 (br s, 1H), 7.47-7.53 (m, 2H), 7.63-7.66 (m, 1H), 7.70-7.73 (m, 2H) 8.00 (d, 1H), 8.53 (br s, 1H), 10.95 (s, 1H); m/z: ES$^+$ [M+H]$^+$ 444.

Example 6

N-[6-[(3R)-3-(Pyridazin-3-ylamino)pyrrolidin-1-yl]pyridazin-3-yl]-2-[2-(trifluoromethoxy)phenyl]acetamide

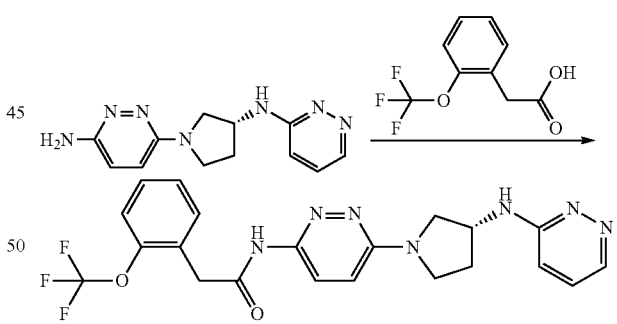

2-[2-(Trifluoromethoxy)phenyl]acetic acid (0.04 g, 0.159 mmol) and 6-[(3R)-3-(pyridazin-3-ylamino)pyrrolidin-1-yl]pyridazin-3-amine (Intermediate 1, 0.04 g, 0.159 mmol) were weighed into a round bottom flask. DMF (1 mL) and HATU (0.06 g, 0.159 mmol) were added and stirred for 5 mins to effect dissolution. Then DIPEA (0.05 g, 0.398 mmol) was added in one portion and the mixture was allowed to stir at room temperature for 15 hours. The solvent was removed under reduced pressure and was absorbed onto silica and purified by flash column chromatography gradient eluting with 100% DCM up to 10% methanolic ammonia: 90% DCM to elute the title compound as a pale yellow solid (50 mg). LCMS analysis showed that there was a 5% impurity of hydroxy benzotriazole (HOBt). The solid was dissolved in DMSO (1 mL) and purified by mass directed LCMS (Waters C18 SunFire column, 5 µm pore size, 4.60 mm diameter, 50 mm length). The flow rate was 25 mL/min and the mobile phases of water and acetonitrile contained 0.1% formic acid. The elution was started at 95% water: 5% acetonitrile which was held for 1.5 minutes ramping up to 5% water:95% acetonitrile over 10 minutes. This was then held for 30 seconds, such that the complete length of the run was 12 minutes. The appropriate fractions were added to an SCX cartridge and washed with methanol, and then the title compound was eluted with 2M ammonia in methanol. The solvent was evaporated under reduced pressure to provide N-[6-[(3R)-3-(pyridazin-3-ylamino)pyrrolidin-1-yl]pyridazin-3-yl]-2-[2-(trifluoromethoxy)phenyl]acetamide as a white solid (0.038 g, 51%). $^1$H NMR (400 MHz, DMSO, 21.8° C.) δ 2.01-2.08 (1H, m), 2.28-2.37 (1H, m), 3.42 (dd, 1H), 3.52-3.64 (m, 2H), 3.81 (dd, 1H), 3.85 (s, 2H), 4.60-4.63 (m, 1H), 6.81 (dd, 1H), 6.98 (d, 1H), 7.13 (d, 1H), 7.24 (dd, 1H), 7.32-7.43 (m, 3H), 7.47-7.49 (m, 1H) 7.95 (d, 1H), 8.45 (dd, 1H), 10.90 (s, 1H); m/z: ES$^+$ [M+H]$^+$ 460.

Intermediate 1

6-[(3R)-3-(pyridazin-3-ylamino)pyrrolidin-1-yl]pyridazin-3-amine

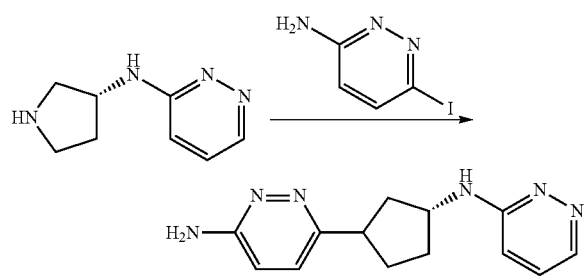

(2S,4R)-4-Hydroxypyrrolidine-2-carboxylic acid (0.240 g, 1.83 mmol) was added to a solution of (R)—N-(pyrrolidin-3-yl)pyridazin-3-amine (Intermediate 2, 1.5 g, 9.13 mmol) in dry DMSO (12 mL). Then, in turn, were added copper(I) iodide (0.174 g, 0.91 mmol) followed by 6-iodopyridazin-3-amine (Intermediate 3, 2.62 g, 11.88 mmol) and then potassium phosphate (5.82 g, 27.40 mmol). The reaction mixture was then stirred at r.t. under nitrogen for 24 h. The mixture was diluted with MeOH (12 mL) and water (12 mL). The mixture was neutralised with acetic acid, causing a solid to precipitate, which was collected. The liquid layer was decanted for use in the SCX step and the solid washed with MeOH (2×5 mL), the wash layers being combined with the liquid layer from the previous step and being passed through a 20 g SCX cartridge, flushing with MeOH to remove impurities followed by a 1N solution of ammonia in MeOH to bring off the product. The solvent was evaporated under reduced pressure and the residue was purified by FCC, elution gradient 0 to 10% (7N ammonia in MeOH) in DCM. Pure fractions were evaporated to dryness to afford 6-[(3R)-3-(pyridazin-3-ylamino)pyrrolidin-1-yl]pyridazin-3-amine (1.220 g, 52%) as a gum.
$^1$H NMR (400 MHz, DMSO, 30° C.) δ 1.99 (1H, m), 2.22-2.37 (1H, m), 3.44 (1H, m), 3.53 (1H, m), 3.73 (1H, m), 4.05 (1H, m), 4.55-4.66 (1H, m), 5.43 (2H, s), 6.75 (1H, d), 6.79-6.88 (2H, m), 7.04 (1H, d), 7.23 (1H, dd), 8.44 (1H, dd); m/z: ES+ [M+H]+ 258.

Intermediate 2

N-[(3R)-pyrrolidin-3-yl]pyridazin-3-amine

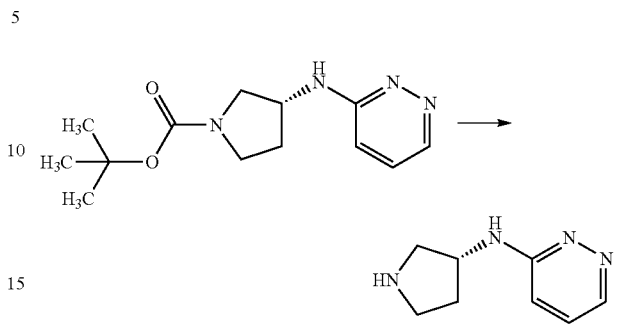

TFA (12.00 mL) was added to tert-butyl (3R)-3-(pyridazin-3-ylamino)pyrrolidine-1-carboxylate (Intermediate 3, 2.2 g, 8.32 mmol) in DCM (80 mL) and the yellow solution left to stir at ambient temperature for 1 h. The crude product was purified by ion exchange chromatography, using an SCX column. The desired product was eluted from the column using 7M ammonia/MeOH and pure fractions were evaporated to dryness to afford N-[(3R)-pyrrolidin-3-yl]pyridazin-3-amine (1.39 g, 102%) as a yellow gum.
$^1$H NMR (400 MHz, DMSO, 30° C.) δ 1.57 (1H, m), 1.91-2.1 (1H, m), 2.61 (1H, m), 2.78 (1H, m), 2.89 (1H, m), 3.04 (1H, m), 4.14-4.38 (1H, m), 6.76 (2H, m), 7.20 (1H, d), 8.40 (1H, d); m/z: ES$^+$ [M+H]$^+$ 165.

Intermediate 3 tert-butyl (3R)-3-(pyridazin-3-ylamino)pyrrolidine-1-carboxylate

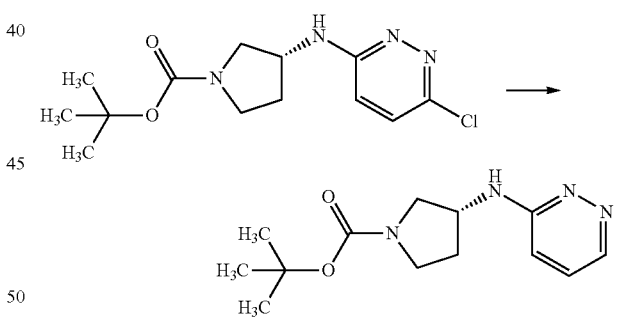

Palladium 10% on C (0.810 g, 7.61 mmol) was added to tert-butyl (3R)-3-[(6-chloropyridazin-3-yl)amino]pyrrolidine-1-carboxylate (Intermediate 5, 7 g, 15.23 mmol) and ammonium formate (14.40 g, 228.44 mmol) in ethanol (200 mL) at 21° C. under nitrogen. The resulting mixture was stirred at reflux for 3 h. The reaction mixture was filtered through celite and washed through with MeOH/DCM. The crude product was purified by FCC, elution gradient 0 to 15% MeOH in DCM. Pure fractions were evaporated to dryness to afford tert-butyl (3R)-3-(pyridazin-3-ylamino)pyrrolidine-1-carboxylate (2.230 g, 55%) as a yellow solid.
$^1$H NMR (400 MHz, DMSO, 30° C.) δ 1.40 (9H, s), 1.86 (1H, m), 2.16 (1H, m), 3.29-3.46 (3H, m), 3.60 (1H, m), 4.43 (1H, m), 6.81 (1H, dd), 7.00 (1H, d), 7.24 (1H, dd), 8.45 (1H, dd); m/z: ES$^+$ [M+H]$^+$ 265.

Intermediate 4

6-iodopyridazin-3-amine

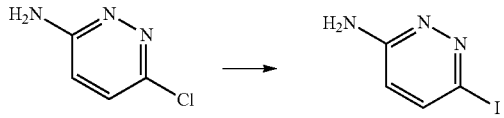 [SMILES: Nc1ccc(Cl)nn1 ; Nc1ccc(I)nn1]

6-Chloropyridazin-3-amine (3.7 g, 28.56 mmol) was charged to a 100-mL round-bottom flask equipped with a reflux condenser and magnetic stir-bar. To this was then added hydrogen iodide (57 wt % solution in water, 20 mL, 265.96 mmol), and the resulting dark-brown solution was heated to gentle reflux and left to stir for 6 h. The mixture was cooled to r.t. and the crude solid was filtered off, rinsing the reaction vessel onto the filter cake with a further volume of ice cold water (2×~30 mL). The resulting solid was partitioned between ethyl acetate and 2N aq. sodium hydroxide, the organic layer was washed with aq. brine, dried, filtered and evaporated under reduced pressure to yield 6-iodopyridazin-3-amine (4.10 g, 65%) as a solid. $^1$H NMR (400 MHz, DMSO, 27° C.) δ 6.52 (2H, s), 6.55 (1H, d), 7.54 (1H, d).

Intermediate 5 tert-butyl (3R)-3-[(6-chloropyridazin-3-yl)amino]pyrrolidine-1-carboxylate

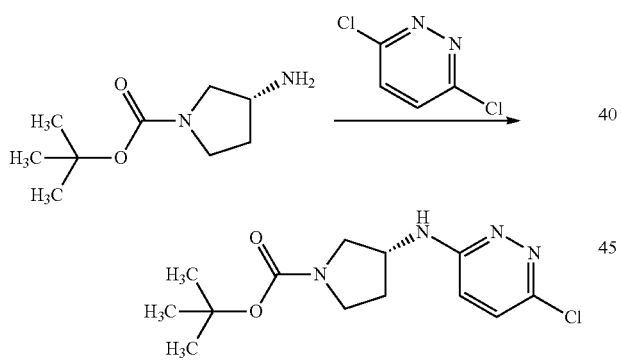

DIPEA (22.44 mL, 128.86 mmol) was added to 3,6-dichloropyridazine (6.40 g, 42.95 mmol), tert-butyl (3R)-3-aminopyrrolidine-1-carboxylate (8 g, 42.95 mmol) in NMP (150 mL) at 21° C. under nitrogen. The mixture was stirred at 150° C. for 24 h. The reaction mixture was diluted with EtOAc (400 mL), and washed twice with water (200 mL). The organic layer was dried over Na$_2$SO$_4$, filtered and adsorbed onto silica. The crude product was purified by FCC, elution gradient 20 to 70% EtOAc in heptane. Pure fractions were evaporated to dryness to afford tert-butyl (3R)-3-[(6-chloropyridazin-3-yl)amino]pyrrolidine-1-carboxylate (7.10 g, 55%) as pink/red solid. $^1$H NMR (400 MHz, DMSO, 30° C.) δ 1.40 (9H, s), 1.86 (1H, m), 2.15 (1H, m), 3.16 (1H, m), 3.33-3.49 (2H, m), 3.59 (1H, m), 4.38 (1H, m), 6.91 (1H, d), 7.31 (1H, d), 7.38 (1H, d); m/z: ES$^-$ [M-H]$^-$ 297.

Intermediate 6

2-[3-(Difluoromethoxy)phenyl]-2-methoxyacetic acid

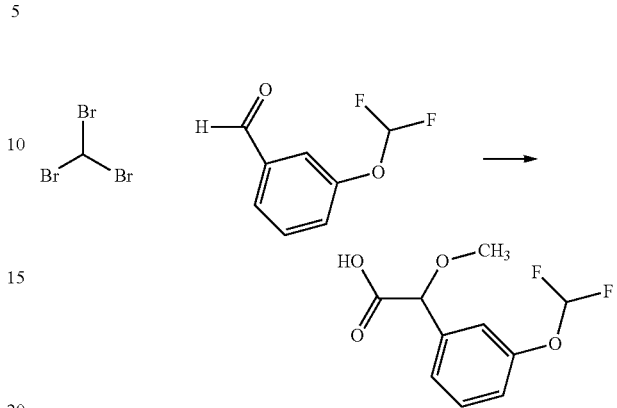

Solid potassium hydroxide (5.38 g, 95.86 mmol) was added portionwise over 1 h to a stirred solution of 3-(difluoromethoxy)benzaldehyde (3 g, 17.43 mmol), bromoform (1.829 mL, 20.91 mmol) and anhydrous MeOH (25 mL) at 0° C. The cooling bath was removed and the reaction was stirred at ambient temperature (a strong exothermic reaction started). The reaction was left stirring overnight. The inorganic solid was filtered off and washed with MeOH. The filtrate was concentrated in vacuo to small volume, diluted with water (100 mL) and washed twice with Et$_2$O (2×50 mL) and acidified to pH 2 by slow addition of 37% HCl. The mixture was extracted with ethyl acetate (3×50 mL). The organic layer was dried over Na$_2$SO$_4$, filtered and evaporated to afford crude product. The crude product was purified by FCC, elution gradient 0 to 60% ethyl acetate in heptane with 0.5% of formic acid. Pure factions were evaporated to dryness to afford 2-[3-(difluoromethoxy)phenyl]-2-methoxyacetic acid (1.710 g, 42%) as a gum.

$^1$H NMR (400 MHz, DMSO-d6, 30° C.) δ 3.33 (3H, s), 4.82 (1H, s), 7.16 (2H, dd), 7.28 (1H, d), 7.23 (1H, t), 7.42-7.47 (1H, m), 12.93 (1H, s); m/z: ES$^-$ [M-H]$^-$ 231.25.

Intermediate 7

2-Methoxy-2-[3-(trifluoromethoxy)phenyl]acetic acid

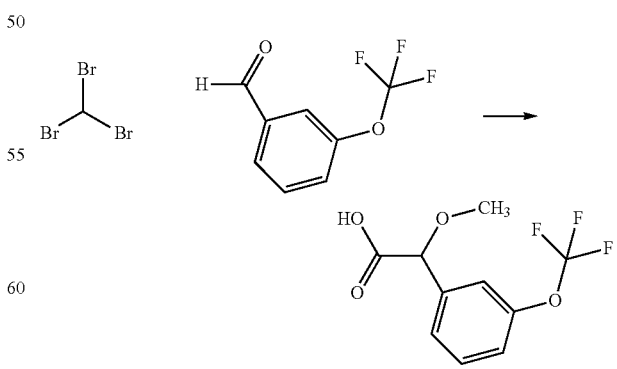

A solution of potassium hydroxide (1.851 g, 33.00 mmol) in MeOH (10 mL) was added over 2 h in small portions to a stirred mixture of 3-(trifluoromethoxy)benzaldehyde (1.141 g, 6 mmol) and bromoform (0.630 mL, 7.20 mmol) in MeOH (5.00 mL) at 0° C. The mixture was then allowed to warm to r.t. and left to stir overnight. A white precipitate had formed in the reaction mixture. The reaction was left to stand overnight. Solids were filtered under reduced pressure, rinsing with MeOH (15 mL). The filtrate solution was evaporated to a thick white paste then re-dissolved in water (50 mL). This was then washed with Et$_2$O (50 mL) and then the aqueous phase was acidified to pH 2 (~5 mL 2M HCl solution) giving a cloudy aqueous layer. The aqueous phase was extracted into ethyl acetate (3×50 mL). The combined organics were dried over anhydrous magnesium sulfate and filtered then solvents were evaporated under reduced pressure to give a clear oil. The crude product was purified by FCC, elution gradient 10 to 50% ethyl acetate in heptane. Pure fractions were evaporated to dryness to afford 2-methoxy-2-[3-(trifluoromethoxy)phenyl]acetic acid (0.832 g, 55%) as a colourless oil.

$^1$H NMR (400 MHz, CDCl$_3$, 30° C.) δ 3.47 (3H, s), 4.81 (1H, s), 7.2-7.24 (1H, m), 7.33 (1H, s), 7.37-7.46 (2H, m); m/z: ES$^-$ [M–H]$^-$ 249.4.

Intermediate 8

2-Methoxy-2-(3-methoxyphenyl)acetic acid

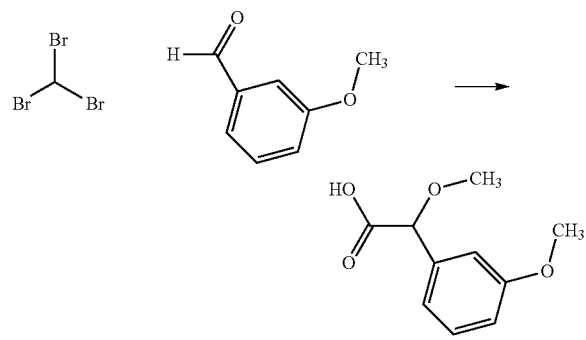

A solution of potassium hydroxide (2.267 g, 40.40 mmol) in MeOH (10 mL) was added over 2 h in small portions to a stirred mixture of 3-methoxybenzaldehyde (1 g, 7.34 mmol) and bromoform (0.771 mL, 8.81 mmol) in MeOH (5.00 mL) at 0° C. The mixture was then allowed to warm to r.t. and left to stir overnight. The solids were filtered under reduced pressure, rinsing the solids with MeOH (15 mL). The filtrate was evaporated to a thick white paste then re-dissolved in water (50 mL). This was then washed with Et$_2$O (50 mL) and then the aqueous portion was acidified to pH=2 (~5 mL 2M HCl solution). The aqueous phase was then extracted with ethyl acetate (3×, 50 mL). The combined organics were dried over anhydrous magnesium sulfate and filtered then solvents were evaporated under reduced pressure to give 2-methoxy-2-(3-methoxyphenyl)acetic acid as a yellow oil (1.4 g, 97%) that was used without further purification.

$^1$H NMR (400 MHz, DMSO-d6, 30° C.) δ 3.18 (3H, s), 3.75 (3H, s), 4.74 (1H, s), 6.82-7.05 (3H, m), 7.29 (1H, m), 12.78 (1H, s).

Biological Assays

The following assays were used to measure the effects of the compounds of the present invention: a) GLS Enzyme Potency Assay; b) GLS Cell Potency Assay; c) GLS Cell Proliferation Assay. During the description of the assays, generally:

i. The following abbreviations have been used: CO$_2$=Carbon dioxide; DMEM=Dulbecco's Modified Eagle Medium; DMSO=Dimethyl sulphoxide; EDTA=Ethylenediaminetetraacetic acid; EGTA=Ethylene glycol tetraacetic acid; FCS=Foetal calf serum; h=Hour(s); NBS=Non-binding surface; SDS=Sodium dodecyl sulphate; TRIS=Tris(Hydroxymethyl)aminomethane.

ii. IC$_{50}$ values were calculated using a smart fitting model in Genedata. The IC$_{50}$ value was the concentration of test compound that inhibited 50% of biological activity.

Assay a): GLS Enzyme Potency Assay

A Glutamate Oxidase/AmplexRed coupled assay was used to measure the ability of compounds to bind to and inhibit the activity of GLS1 in vitro. 6His tagged GLS protein (amino acids 63-669) expressed in E. Coli was purified and stored at −80° C. in aliquots. GLS1 was diluted to 2×working concentration and incubated at r.t. to allow the tetrameric/dimeric forms to reach steady state. Assay measurements were performed in buffer comprising 50 mM TRIS pH 7.8, 100 mM NaPO$_4$, pH 7.8, 0.001% v/v Tween20. Purified recombinant GLS1 protein was diluted in assay buffer to 12 nM and pre-incubated at r.t. for 30 minutes. Test compounds were prepared by dilution in 100% DMSO to give the correct dose range for 12 point concentration response and an appropriate volume (2.5-60 nl) dispensed into 384 well micro assay plates (Greiner product code 784900) using a Labcyte Echo 555 acoustic dispenser. DMSO concentration was maintained at 2% by back filling with DMSO solution. 3 μL of diluted GLS1 protein (12 nM) was then dispensed into each well using a BioRaptr automated dispenser (Beckman-Coulter) and incubated for 15 minutes at r.t. 3 μl of 100 mM glutamine diluted in assay buffer was then added and the reaction incubated at r.t. for 60 minutes. The reaction was then stopped by addition of 45 μM 6-(2-bromoethynyl)-2,3-dimethyl-quinazolin-4-one, 75 μM Amplex Red, 0.375 units/mL Horseradish Peroxidase, 0.12 units/mL Glutamate Oxidase in 100 mM TRIS pH7.5. After 30 minutes at room temp in the dark, plates were read on a Perkin Elmer EnVision using 535/590 nm optic filters and raw data analysed using Genedata to generate IC$_{50}$ values. An artefact version of the assay where the 6His tagged GLS protein and glutamine were replaced with assay buffer was also used to rule out non specific effects on the assay components.

Assay b): GLS Cell Potency Assay

Compounds were assessed for their potential to inhibit cellular GLS activity by use of a PC3 coupled assay measuring cellular glutamate depletion. Test compounds were prepared by dilution in 100% DMSO to give the correct dose range for 12 point concentration response and an appropriate volume (5-120 nl) dispensed into 384 well micro assay plates (Corning product code 3712) using a Labcyte Echo 555 acoustic dispenser. DMSO concentration was maintained at 0.3% by back filling with DMSO solution. PC3 cells were grown in phenol free DMEM, 10% dialyzed FCS, 2 mM glutamine and following dispersal by trypsinisation were plated at 5.6×10$^3$ cells per well in 40 μl of growth medium directly into the 384 well assay plates containing dispensed compound. After incubation for 6 h at 37° C., 5% CO$_2$ growth media was aspirated and cells lysed in 15 μl of buffer containing 10 mM TRIS pH7.4, 100 mM NaCl, 1 mM EDTA, 1 mM EGTA, 1 mM NaF, 20 mM Na$_4$P$_2$O$_7$, 2 mM Na$_3$VO$_4$, 1% Triton X-100, 10% glycerol, 0.1% SDS and 0.5% deoxycholate. 4 µl Of cell lysate was then transferred to a 384 well NBS plate (Corning product code 3575) and 35 µl of 27.5 µM Amplex Red, 0.1375 U/mL Horseradish Peroxidase, 0.044 U/mL glutamate oxidase, 100 mM TRIS pH7.5 was added. After 30 minutes at room temp in the dark, plates were read on a Perkin Elmer EnVision using 535/590 nm optic filters and raw data analysed using proprietary software to generate $IC_{50}$ values.

Assay c): GLS Cell Proliferation Assay

The ability of compounds to inhibit cell growth was measured using a 384 well plate NCI-H1703 cell proliferation assay. NCI-H1703 cells were grown in phenol red free RPMI1640, 10% FCS and 2 mM glutamine and seeded at a density of 750 cells per well in 40 µl of growth medium into clear-bottom 384 well assay plates (Corning product code 3712) and incubated for 24 h at 37° C., 5% $CO_2$. Test compounds were prepared by dilution in 100% DMSO to give the correct dose range for 12 point concentration response and an appropriate volume (5-120 nl) dispensed directly into the assay plates containing plated cells. DMSO concentration was maintained at 0.3% by back filling with DMSO solution. Plates were incubated for 5 days at 37° C., 5% $CO_2$, Sytox Green and Saponin added to final concentration of 2 µM and 0.25% respectively and incubated for 6 h prior to analysis. Plates were read on an Acumen eX3 (TTP Labtech) using 488 nm excitation and FITC filter set (500-530 nm) for emission. $IC_{50}$ values were calculated by curve fitting to max inhibition of day zero growth using GeneData software analysis.

The potency of the Examples of the invention in assays a)-c) are shown in Table 1. Results may be an average of multiple tests, and different Examples may have been tested in different numbers of tests. Results are rounded to a certain number of decimal places.

TABLE 1

Potency Data for Examples 1-4 in Assays a)-c)

| Example | Assay a) GLS Enzyme Potency Assay $IC_{50}$ (µM) | Assay b) GLS Cell Potency Assay $IC_{50}$ (µM) | Assay c) GLS Cell Proliferation Assay (µM) |
|---|---|---|---|
| 1 | 0.0247 | 0.001 | 0.009 |
| 2 | 0.0957 | 0.001 | 0.011 |
| 3 | 0.0298 | 0.001 | 0.003 |
| 4 | 0.0309 | 0.007 | 0.043 |
| 5 | 0.0306 | 0.001 | 0.003 |
| 6 | 0.0252 | 0.001 | 0.012 |

The invention claimed is:

1. A compound of Formula (I):

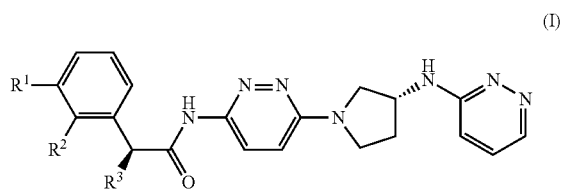

(I)

or a pharmaceutically acceptable salt thereof, where:
$R^1$ is hydro, methoxy, difluoromethoxy or trifluoromethoxy;
$R^2$ is hydro, methoxy, trifluoromethoxy or trifluoromethyl; and
$R^3$ is hydro or methoxy.

2. The compound of Formula (I), or a pharmaceutically acceptable salt thereof, as claimed in claim 1, where $R^1$ is methoxy, difluoromethoxy or trifluoromethoxy.

3. The compound of Formula (I), or a pharmaceutically acceptable salt thereof, as claimed in claim 2, where $R^1$ is methoxy.

4. The compound of Formula (I), or a pharmaceutically acceptable salt thereof, as claimed in claim 1, where $R^2$ is hydro.

5. The compound of Formula (I), or a pharmaceutically acceptable salt thereof, as claimed in claim 1, where $R^2$ is methoxy.

6. The compound of Formula (I), or a pharmaceutically acceptable salt thereof, as claimed in claim 1, where $R^3$ is methoxy.

7. The compound of Formula (I), or a pharmaceutically acceptable salt thereof, as claimed in claim 1, where $R^3$ is hydro.

8. The compound of Formula (I), or a pharmaceutically acceptable salt thereof, as claimed in claim 1, where:
$R^1$ is methoxy, difluoromethoxy or trifluoromethoxy;
$R^2$ is hydro; and
$R^3$ is methoxy.

9. The compound of Formula (I), or a pharmaceutically acceptable salt thereof, as claimed in claim 1, where:
$R^1$ is hydro;
$R^2$ is methoxy, trifluoromethoxy or trifluoromethyl; and
$R^3$ is hydro.

10. The compound of Formula (I), a compound of Formula (I), or a pharmaceutically acceptable salt thereof, where the compound of Formula (I) is selected from:
(2S)-2-[3-(Difluoromethoxy)phenyl]-2-methoxy-N-[6-[(3R)-3-(pyridazin-3-ylamino)pyrrolidin-1-yl] pyridazin-3-yl]acetamide;
(2S)-2-[3-(Trifluoromethoxy)phenyl]-2-methoxy-N-[6-[(3R)-3-(pyridazin-3-ylamino)pyrrolidin-1-yl] pyridazin-3-yl]acetamide;
(2S)-2-Methoxy-2-(3-methoxyphenyl)-N-[6-[(3R)-3-(pyridazin-3-ylamino)pyrrolidin-1-yl]pyridazin-3-yl] acetamide;
2-(2-Methoxyphenyl)-N-[6-[(3R)-3-(pyridazin-3-ylamino)pyrrolidin-1-yl]pyridazin-3-yl]acetamide;
N-[6-[(3R)-3-(Pyridazin-3-ylamino)pyrrolidin-1-yl] pyridazin-3-yl]-2-[2-(trifluoromethyl)phenyl]acetamide; and
N-[6-[(3R)-3-(Pyridazin-3-ylamino)pyrrolidin-1-yl] pyridazin-3-yl]-2-[2-(trifluoromethoxy)phenyl]acetamide.

11. A pharmaceutical composition which comprises a compound of Formula (I), or a pharmaceutically acceptable salt thereof, as claimed in claim 1, and at least one pharmaceutically acceptable diluent or carrier.

* * * * *